United States Patent [19]
Monson et al.

[11] Patent Number: 5,674,219
[45] Date of Patent: Oct. 7, 1997

[54] ELECTROSURGICAL SMOKE EVACUATOR

[75] Inventors: Donald R. Monson, West St. Paul; Daniel E. Adamek, Roseville, both of Minn.

[73] Assignee: Donaldson Company, Inc., Minneapolis, Minn.

[21] Appl. No.: 319,265

[22] Filed: Oct. 6, 1994

[51] Int. Cl.$^6$ .................................................. A61B 17/39
[52] U.S. Cl. ............................. 606/45; 606/49; 604/22
[58] Field of Search ......................... 606/41, 42, 45, 606/49; 604/22, 35

[56] References Cited

U.S. PATENT DOCUMENTS

| | | |
|---|---|---|
| 3,401,690 | 9/1968 | Martin ........................ 604/22 |
| 3,540,432 | 11/1970 | Ayre .......................... 604/35 |
| 4,619,672 | 10/1986 | Robertson . |
| 4,719,914 | 1/1988 | Johnson . |
| 4,735,603 | 4/1988 | Goodson et al. . |
| 4,826,513 | 5/1989 | Stackhouse et al. . |
| 4,919,129 | 4/1990 | Weber, Jr. et al. . |
| 4,960,419 | 10/1990 | Rosenberg . |
| 5,039,494 | 8/1991 | Martin et al. . |
| 5,047,072 | 9/1991 | Wertz et al. . |
| 5,055,100 | 10/1991 | Olsen . |
| 5,061,268 | 10/1991 | Fleenor . |
| 5,071,418 | 12/1991 | Rosenbaum . |
| 5,085,657 | 2/1992 | Ben-Simhon . |
| 5,108,389 | 4/1992 | Cosmescu . |
| 5,108,474 | 4/1992 | Riedy et al. . |
| 5,154,709 | 10/1992 | Johnson . |
| 5,160,334 | 11/1992 | Billings et al. . |
| 5,186,714 | 2/1993 | Boudreault et al. . |
| 5,192,267 | 3/1993 | Shapira et al. . |
| 5,199,944 | 4/1993 | Cosmescu . |
| 5,224,944 | 7/1993 | Elliot ........................ 606/45 |
| 5,226,939 | 7/1993 | Nicolas et al. . |
| 5,234,428 | 8/1993 | Kaufman . |
| 5,242,442 | 9/1993 | Hirschfield . |
| 5,242,474 | 9/1993 | Herbst et al. . |
| 5,269,781 | 12/1993 | Hewell, III . |
| 5,318,516 | 6/1994 | Cosmescu . |
| 5,431,650 | 7/1995 | Comescu ...................... 606/45 |

FOREIGN PATENT DOCUMENTS 0 447 121 A  9/1991  European Pat. Off. .

OTHER PUBLICATIONS

J.S. Calder et al., *Annals of the Royal College of Surgeons of England*, "Smoke Evacuation During Surgery," pp. 854–855 (1992) vol. 74, 370.

F.H. Ernst, *J Oral Maxillofac Surg*, "Potential Hazards of Vaporized Byproducts: A Need for Precautions," 50:313, 1992.

J.E. Gatti et al., *Plastic and Reconstructive Surgery*, "The Mutagenicity of Electrocautery Smoke,"0 and Discussion, pp. 781–786 (May 1992).

A. L. London et al., *Journal of Engineering for Power*, "Oblique Flow Headers for Heat Exchangers," pp. 271–286, Jul. 1968.

B.L. Wenig et al., *Lagers in Surgery and Medicine*, "Effects of Plume Produced by the Nd:YAG Laser and Electrocautery on the Respiratory System", 13:242–245 (1993).

AirSafe™ Smoke Filtration System Brochure, Stackhouse, Inc., Riverside, CA 92507, 20M Jan. 1991.

*ECRI*, "Smoke Evacuation Systems, Surgical," pp. 1–14 (1993).

Primary Examiner—Lee S. Cohen
Attorney, Agent, or Firm—Merchant, Gould, Smith, Edell, Welter & Schmidt, P.A.

[57] ABSTRACT

A smoke evacuator and a system for surgical devices, such as electrocautery scalpels and laser surgical devices. Evacuator is geometrically designed to permit retrofit to existing electrocautery scalpels, and includes a radiused inlet to minimize noise and a stand off to prevent unintentional tissue suck down. The system optimizes suction flow rate, inlet diameter, and inlet distance so as to provide efficient evacuation while permitting good visibility. An automatic smoke evacuation system is also provided which switches the smoke evacuation on or off depending upon whether a current is sensed in the power cord to the electrosurgical device.

15 Claims, 6 Drawing Sheets

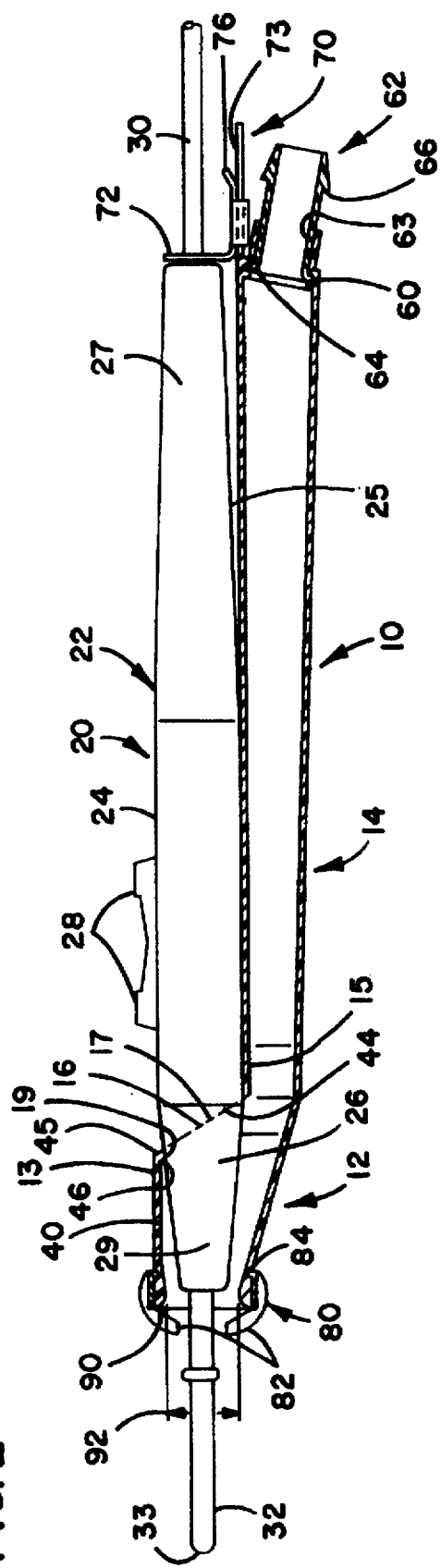
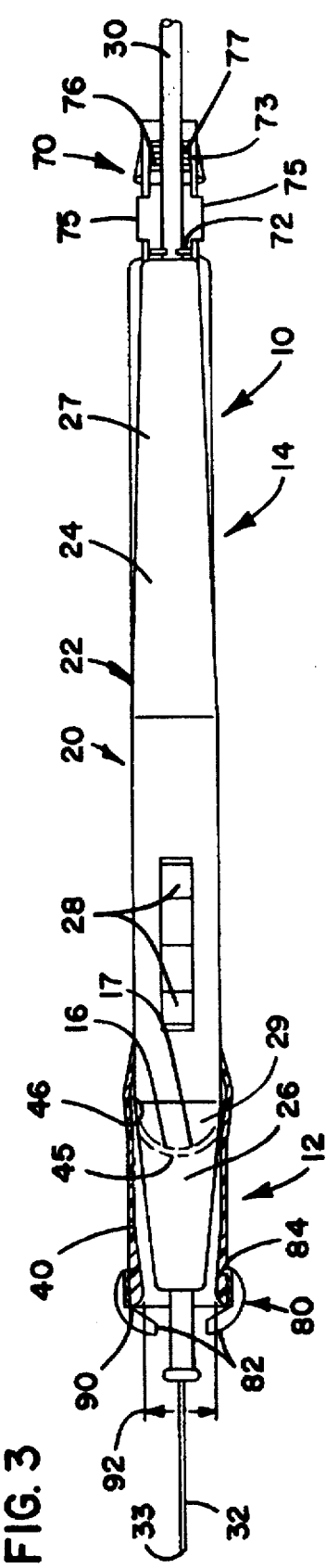
FIG. 2
FIG. 3

ELECTROSURGICAL SMOKE EVACUATOR

FIELD OF THE INVENTION

This invention relates generally to evacuation of smoke and fumes during surgery when surgical instruments, such as electrocautery scalpels or laser surgical devices, are employed. More particularly, it relates to an adaptable smoke evacuator and a system for smoke evacuation during such procedures.

BACKGROUND OF THE INVENTION

Modern surgical techniques involve a variety of surgical instruments which generate smoke, fumes and/or aerosols. The most common examples of such devices include electrocautery scalpels and laser surgical devices used in many forms of open and closed (endoscopic) surgeries.

During such procedures, as for example when cutting or cauterizing tissue with an electrocautery scalpel, a plume is generated. This plume causes a variety of problems. The visible smoke in the plume can impair the view of the surgeon, and an assistant is often necessary to clear the operative field using suction. The fumes also cause a noxious odor which is a source of irritation to the surgeon, surgical assistants and, during surgeries with local anesthesia, the patient. Additionally, recent studies have raised concerns regarding the potential health hazards which the plume can pose to surgical personnel, including carcinogens and viruses such as HIV. During electrocautery procedures the tissue is burned, and cell particles are released which may become entrained in the plume. These particles can potentially carry bacteria and viruses. Concerns have also been raised regarding the respiratory hazards (e.g. carcinogenic) which the smoke itself may pose. In the United States, both the National Institute of Occupational Safety and Health (NIOSH) and the American Association of Operating Room Nurses (AAORN) have recommended that this pollutant be removed as a standard operating room procedure.

Smoke evacuators are known in the art. While smoke evacuation in the past has generally been done with an evacuator separate from the surgical instrument (usually held by an assistant to the surgeon), this application relates to evacuators which are attached to or integral with the instrument. The vast majority of these devices are built into the scalpel, and thus would require a purchaser to buy the entire assembly as a unit. Examples include U.S. Pat. Nos. 4,719,914, 5,242,442 and 5,269,781. These devices generally have an inlet in close proximity to the blade of the scalpel and a vacuum source connected thereto. The inlet is positioned either along side the blade, as in the '442 patent, or generally coaxial with the blade, as in the '914 patent.

A more limited number of smoke evacuators are known which are designed to be connected (i.e., "retrofit") to an existing electrocautery scalpel. Examples include U.S. Pat. Nos. 5,055,100, 5,085,657 and 5,154,709. These devices, however, suffer from a variety of shortcomings. For example, the device of the '100 patent would not eliminate smoke as efficiently as one with a co-axial inlet. Also, due to the placement of the vacuum tubing, this device would be impaired for a left-handed user. Both the devices of the '657 and '709 patents would cause difficulties in operating the control buttons due to the placement of the vacuum hose. The '709 device, in particular, would cause manipulation problems as a result of the placement of the hose attachment on the front end of the scalpel. These two devices also place the inlet too close to the distal tip of the blade, thereby causing visibility problems as well as the possibility that the inlet could unintentionally suck down on and damage tissue.

Another problem with smoke evacuation systems is the amount of noise which they generate. An undue noise level could interfere with conversation between surgical personnel as well as cause irritation and fatigue after prolonged exposure. The inlets of prior art evacuators typically have a sharp leading edge, which not only results in significant noise due to flow separation, but also causes valuable pressure loss in the system. Also, prior art systems which employ a stand alone blower rather than the surgical room wall suction, do not sufficiently minimize noise through acoustic treatment or otherwise.

Yet another problem associated with smoke evacuators is that the inlet can be unintentionally sucked down onto tissue due to its proximity to the blade, which can cause trauma to the tissue. This is particularly a concern during procedures, such as those deep into a cavity, where there is substantial other tissue in the area being operated upon. None of the prior art devices appear to address this problem in the geometric design of the evacuator.

The design of smoke evacuators involves a trade off between efficient evacuation and other considerations, such as visibility problems and the potential for unintentional suck down due to the placement of the inlet relative to the blade. The most important parameters which affect these considerations include the size and shape of the inlet, the distance of the inlet from the distal tip of the blade, and the vacuum flow rate. A smaller inlet and farther distance improves visibility but requires a higher vacuum flow rate, while a larger inlet and decreased distance reduces the necessary flow rate but hinders visibility. Most prior art evacuators are connected to surgical room wall suction, which in the United States provides a maximum vacuum flow rate of approximately 3.0 cubic feet per minute (85 l.p.m.). This is insufficient to exhaust an acceptable amount of smoke without placing the inlet too close to the distal tip of the blade. Prior art systems have not achieved a proper balance between these relevant factors to achieve efficient evacuation while maintaining good visibility for the surgeon.

A feature found in some prior art smoke evacuation systems is to switch the suction to the evacuator on or off depending upon whether the electrosurgical device is being used. Examples include U.S. Pat. Nos. 5,108,389 and 5,160,334. These systems also include a mechanism for delaying the deactivation of the smoke evacuator for a period of time after the surgical device is turned off so as to evacuate residual smoke. Both of these systems, however, incorporate the switching mechanism into the circuitry of the power controller for the electrosurgical device. With such a design, one must either buy the entire unit or modify the power controller circuitry of an existing system to incorporate the switching mechanism. In either case, to meet certification requirements, this would require that the entire system be re-certified. It does not appear that an automatic smoke evacuation system is known in the prior art which is adaptable to an existing electrosurgical system without modifying the control circuitry.

What has been needed is a smoke evacuator which is adaptable to a variety of electrocautery scalpels, reduces noise and pressure loss, and minimizes suck down on tissue, and a system which provides an appropriate balance between maintaining visibility while achieving efficient evacuation. What has also been needed is an automatic smoke evacuation system which provides an automatic switching mechanism which is adaptable to an existing electrosurgical system without modification to its power control circuitry. Finally, what has been needed is a blower which is acoustically treated to reduce noise, and a simple compact filter designed to eliminate contaminants before the air is recirculated into the operating room.

SUMMARY OF THE INVENTION

According to the present invention, a smoke evacuator and system for evacuating smoke from surgical devices, such as electrocautery scalpels and laser surgical devices, is provided. Although the smoke evacuator of the present invention is intended primarily for attachment to electrocautery scalpels, certain aspects of the system can be used with other surgical devices as well.

In one aspect of the invention, the smoke evacuator comprises a generally tubular nose portion extending over the fore portion of the scalpel and having an inlet generally co-axial with the blade. An offset duct in fluid communication with the nose portion extends at least partially along the lower side of the scalpel toward the aft portion of the scalpel. The nose portion has a fore portion engagement sleeve defining an opening for receiving the fore portion of the scalpel. This opening includes a resilient material for sealing the opening with the fore portion of the scalpel. The evacuator also includes mechanisms for attaching the offset duct to the scalpel and for attaching a vacuum tube to the offset duct.

In another aspect of the invention, the smoke evacuator comprises an annular inlet proximate the blade, vacuum tubing in fluid communication with the inlet, and a mechanism for creating a vacuum through the tubing and in the inlet. The inner side of the annular inlet has a radiused leading edge, with the ratio of the radius to the inlet diameter being about between 0.15 and 0.25.

In yet another aspect of the present invention, the smoke evacuator comprises an annular inlet proximate the blade of the scalpel and a plurality of axially outwardly and radially inwardly turned ribs spaced around the circumference of the annular inlet. These ribs prevent unintentional suck down on tissue in the vicinity of the inlet.

In another aspect of the present invention, the invention comprises a smoke evacuation system for an electrocautery scalpel. The system comprises a smoke evacuator having a generally tubular portion which is generally co-axial with the blade, with the leading edge of the tubular portion being a predetermined distance from the distal tip of the blade. A vacuum in fluid communication with the evacuator provides a suction flow rate of about between 3.0 and 5.0 cubic feet per minute (85 and 140 l.p.m.). The inlet diameter is about between 0.30 and 0.60 inches (0.75 and 1.5 cm.), and the distance between the leading edge of the tubular portion and the distal tip of the blade is about between 1.0 and 1.5 inches (2.0 and 4.0 cm.).

In yet another aspect of the present invention, the invention comprises an automatic smoke evacuation system for a surgical instrument having a power cord, such as an electrocautery scalpel or a laser surgical apparatus. The system comprises a smoke evacuator attached to the surgical instrument and a vacuum in fluid communication with the evacuator. A device senses whether current is flowing through the power cord. A valve is moveable between a first position wherein vacuum flow is provided to the evacuator and a second position wherein it is not. A switch electronically controlled by the current sensing mechanism causes the valve to move to the first position in response to a current being sensed and to the second position in response to no current being sensed.

These and other advantages and features of novelty which characterize the invention are pointed out with particularity in the claims annexed hereto. However, for a better understanding of the invention and its advantages, reference should be made to the drawings which form a further part hereof, and to the accompanying descriptive matter in which there is illustrated and described a preferred embodiment of the invention.

BRIEF DESCRIPTION OF THE FIGURES

FIG. 2 is a partial cross-sectional view of the smoke evacuator shown in FIG. 1 as viewed generally from Section 2—2;

FIG. 3 is a partial cross-sectional view of the smoke evacuator shown in FIG. 1 viewed generally from Section 3—3;

DETAILED DESCRIPTION OF THE PREFERRED EMBODIMENT

Figure 1:
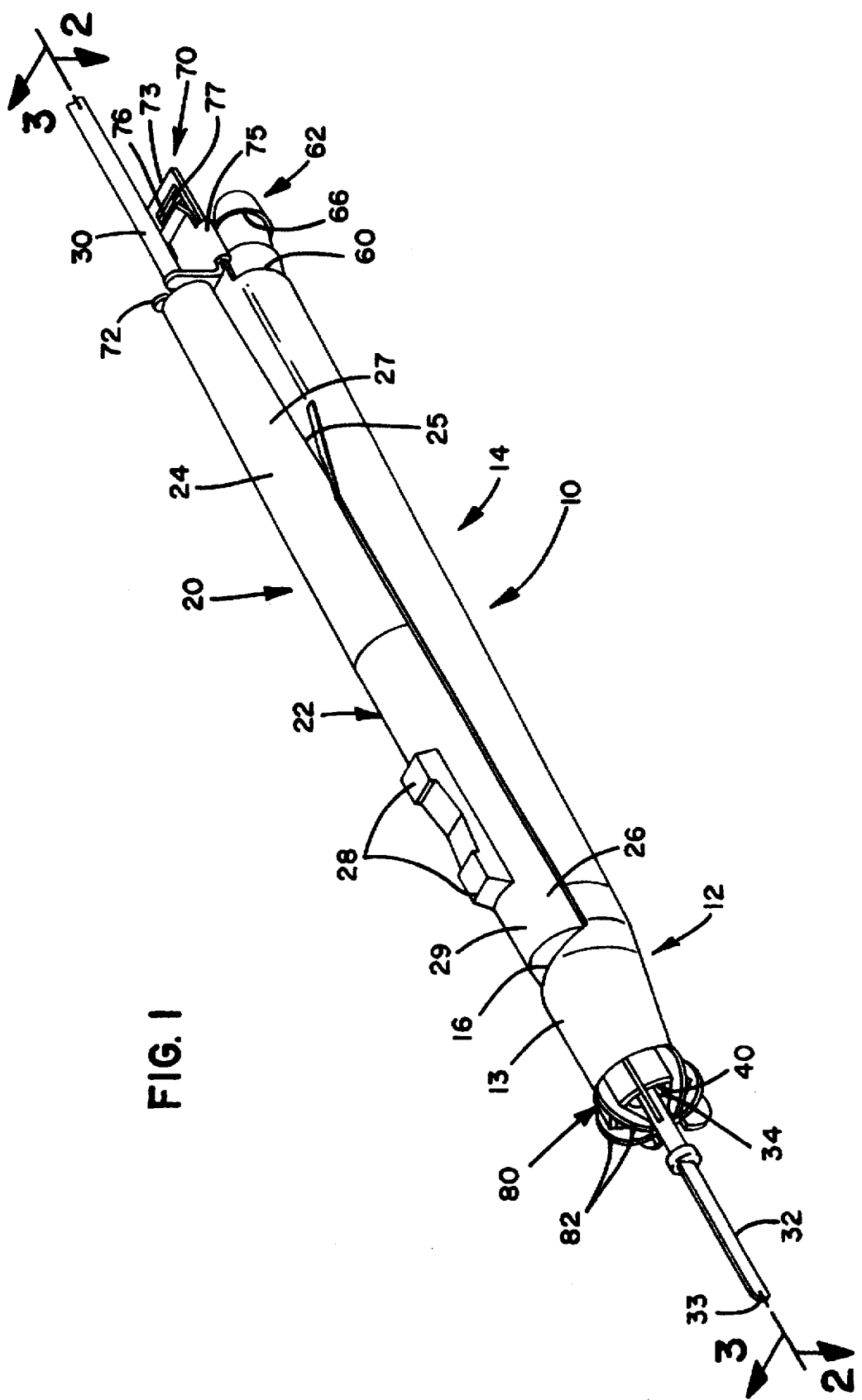
FIG. 1 is a perspective view of a first embodiment of a smoke evacuator according to the present invention, shown attached to an electrocautery scalpel.

Referring now to the drawings wherein like numerals designate like parts, a first embodiment of a smoke evacuator 10 is shown in FIGS. 1–3. Smoke evacuator 10 is designed to be adaptable to a variety of electrocautery scalpels. The evacuator of the present invention was specifically designed to be adaptable to scalpels such as Valleylab E2516, Conmed/Aspen 60-0300-501, Birtcher/Bard 130308, and NDM 30-0100, which are the four leading disposable electrocautery "pencils" sold in the United States. However, the principles of the evacuator could be applied to other electrocautery scalpels as well, including non-disposable scalpels.

Figure 4:
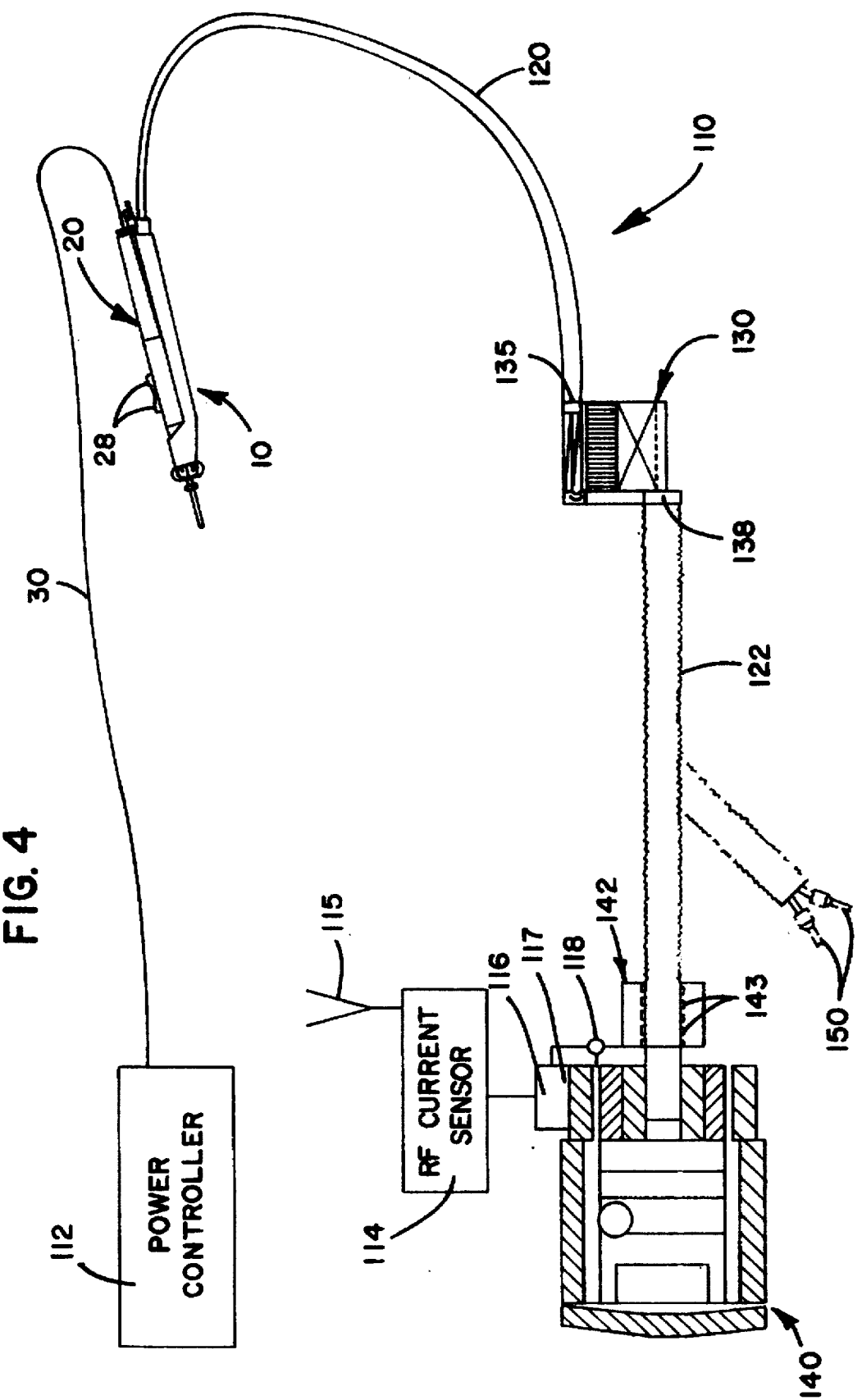
FIG. 4 is a schematic diagram of a smoke evacuation system according to the present invention.

Smoke evacuator 10 is shown attached to such a typical electrocautery scalpel 20. Scalpel 20 includes housing 22 with upper 24 and lower 25 sides and fore 26 and aft 27 portions. Control buttons 28 are provided on an upper side 24. In electrocautery scalpels, typically there is a "cut" button and a "coagulate" button. Power cord 30 extends from the rear of aft portion 27 of scalpel 20, and is typically connected to a power control unit 112, as shown in FIG. 4. Blade 32 extends longitudinally from fore portion 26. In typical designs, blade 32 is received within receptacle 34, and can be replaced with another blade of the same or different length.

Smoke evacuator 10 includes generally tubular nose portion 12 and offset duct 14 extending from nose portion 12 along lower side 25 of scalpel 20 toward aft portion 27 of scalpel 20. Nose portion 12 includes fore portion engagement sleeve 17 defining engagement opening 16 for receiving fore portion 26 of scalpel 20. In the preferred embodiment, sleeve 17 is merely an extension of nose portion 12, and opening 16 extends downwardly from an upper wall 13 of nose portion 12 to an upper wall 15 of offset duct 14. It will be understood, however, that sleeve 17 and opening 16 could be constructed and arranged in a variety of other ways to engage fore portion 26.

Opening 16 includes a resilient material 44 for sealing opening 16 to fore portion 26 of scalpel 20. The seal is primarily a radial seal (some longitudinal force may also add to the seal) between an inner surface 19 of opening 16 (or a gasket as discussed below) and an outer surface 29 of fore portion 26. This general configuration offers several advantages. Primarily, it allows evacuator 10 to be "retrofit" to a scalpel without requiring modifications to the scalpel. Co-axial inlet 40 provides more efficient evacuation of smoke as compared to an inlet which is off to the side of blade 32. The placement of nose portion 12, engagement opening 16 and offset duct 14 provide easy access to control buttons 28 and permit the device to be useable by both left and right-handed users.

Engagement opening 16 is preferably elliptical in shape and slanted so that its upper end is forward of its lower end. This configuration permits the opening to be better adaptable to a variety of scalpels, which may have fore portions with different shapes. It also helps align nose portion 12 with fore portion 26 of scalpel 20.

In the preferred embodiment, nose portion 12 and offset duct 14 are molded as a single plastic part. In order to injection mold them as one part, a "living hinge" can be employed along the bottom so as to split the ecacuator into mirror image halves connected by the hinge. However, they could be constructed using other materials, and/or with two or more parts in varying configurations, so long as fluid communication is provided between them. Because the evacuator 10 is constructed from a plastic with some resiliency (polystyrene) and engagement opening 16 is appropriately contoured, this could provide sufficient sealing of engagement opening 16 to fore portion 26 of scalpel 20. Preferably, however, a separate sealable gasket 44, such as a thin, heat sealable or ultrasonically bondable plastic film or a soft, tacky sealant material, is employed to provide better sealing. Also, such gaskets of varying thickness could be employed to make evacuator 10 better adaptable to different scalpels. Bonding wall 45 on upper perimeter of opening 16 provides a surface for attaching sealable gasket 44, creating a finite gap 46 between the upper portion of nose portion 12 and fore portion 26 of scalpel 20. This gap 46 also creates more uniform flow from around fore portion 26 of scalpel 20 to offset duct 14.

Figure 9:
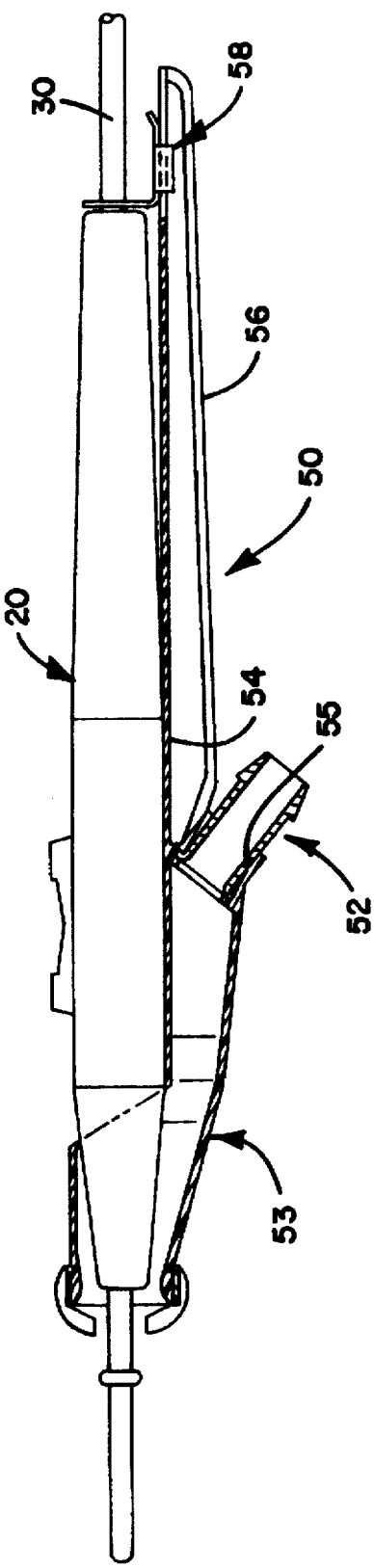
FIG. 9 is a partial cross-sectional view of a second embodiment of a smoke evacuator according to the present invention, shown attached to an electrocautery scalpel.

Offset duct 14 need not extend to the aft end of aft portion 27 of scalpel 20, as in the first embodiment shown in FIGS. 1–3. For example, it may be preferable to terminate offset duct 14 at approximately a center of scalpel 20, as in the second embodiment 50 shown in FIG. 9. This arrangement positions swivel 52 for connection to a vacuum tube close to the center of gravity of scalpel 20. As a result, dexterity may be enhanced by eliminating the drag caused by the vacuum tube extending from the aft end of scalpel 20. In the second embodiment 50, offset duct 53 is attached to scalpel 20 through offset duct upper wall 54 extending to ratchet 58, which attaches to power cord 30 as in the first embodiment 10 (discussed below). Support rib 56 extends between upper wall 54 at its aft end to an upper side of swivel exit port 55.

Exit port 55 is turned downwardly to move swivel 52 and the vacuum tube attached thereto away from scalpel 20, thereby reducing interference.

Referring back to the first embodiment 10 in FIGS. 1 and 2, swivel 62 is attached to aft end 60 of offset duct 14. Swivel 62 is fit into recess 64, which provides sealing. Swivel 62 rotates within recess 64 to prevent torsional forces from being transferred from the vacuum tubing to scalpel 20. Also, exit port 63 is turned slightly downward to minimize interference. This allows the surgeon to better manipulate scalpel 20 when performing surgical procedures. Vacuum tubing is connected to swivel 62 by extending the tubing over the swivel so that tooth 66 engages the tubing. Swivel 62 is preferably made from a polymer material which has a naturally low friction coefficient, such as high density polyethylene, so as to make swivel 62 "self-lubricating."

Offset duct 14 is attached to scalpel 20 via a ratchet mechanism 70 which permits evacuator 10 to be attached to a variety of scalpels. Ratchet 70 includes clip 72, which clips onto power cord 30, and slide 73 having channels 75 and at least one tooth (not shown). Upper wall 16 of offset duct 14 extends past swivel 62 and inserts into channels 75, and includes notches 77 on its upper side for engagement with the tooth of slide 73. Lip 76 is liftable to disengage the tooth from notches 77. This adjustable ratchet mechanism permits evacuator 10 to be able to accommodate a variety of different length scalpels. It will be recognized that numerous other adjustable ratchet arrangements could also be used.

Spaced around the circumference of annular nose inlet 40 is a plurality of ribs 82 which extend radially inwardly from the circumference and axially outwardly from inlet 40. These ribs 82 guard against unintentional suck down on tissue in the vicinity of inlet 40. Ribs 82 are preferably rounded and do not extend all the way to the center of inlet 40 so as to reduce wake turbulence in the region of maximum velocity and therefore the potential for aerodynamic noise. In the preferred embodiment, ribs 82 form a single part 80 or "standoff" which is snapped into recess 84 on the outer side of nose portion 12. It will be understood, however, that ribs 82 could be molded as part of nose inlet 40. Also, it may be preferable to eliminate one or more ribs at the top of standoff 80 so as to improve visibility for the surgeon.

Figure 8:
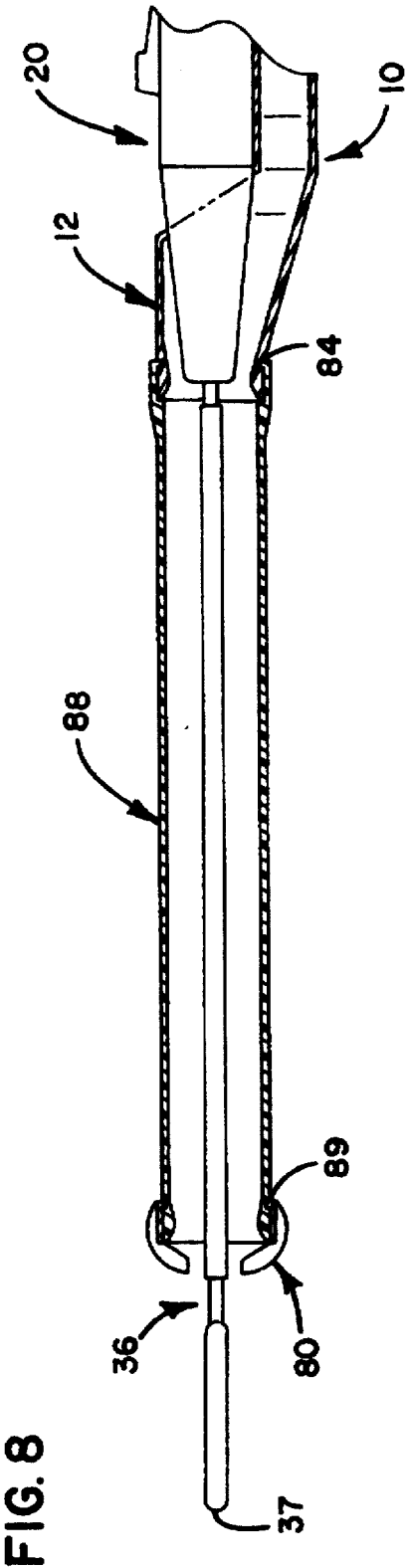
FIG. 8 is a partial cross-sectional view of an inlet extension for a smoke evacuator according to the present invention.

Referring to FIG. 8, nose extension 88 is shown for use with an extended blade 36 on scalpel 20. Extension 88 snaps into recess 84, and includes an identical inlet configuration, with its own recess 89 for receiving standoff 80. Nose extension 88 is preferably sized to position the leading edge of the inlet with respect to blade 36 and blade tip 37 identically as with the conventional short blade.

Referring to FIGS. 2 and 3, inlet 40 has what is referred to as a "Bellmouth" shape so as to reduce flow separation at leading edge 90 and therefore aerodynamic noise and pressure loss. Leading edge 90 is radiused to a specific value which is dependent on inlet diameter 92. Attached flow can be assured when the ratio of the radius of leading edge 90 to inlet diameter 92 is approximately 0.18 or greater. In the preferred embodiment, a ratio of approximately 0.18 (with inlet diameter 92 being approximately 0.45 inches (1.1 cm.)) is chosen so as to maintain attached flow while keeping the total size of inlet 40 as small as possible. Those skilled in the art will recognize that, while the inlet configuration of the present design is intended for a vacuum flow rate of approximately 3.0 to 5.0 cubic feet per minute (85 to 140 l.p.m.), the appropriate ratio and inlet diameter may vary depending upon the flow rate which is employed. For example, the ratio could vary from about between 0.15 and 0.25 within the principles of the invention.

Referring to FIG. 4, a system 110 for smoke evacuation is shown. While the system is designed primarily for use with electrocautery scalpels, certain features of the system could be employed in other applications as well, such as with laser surgery devices.

One of the features of system 110 is to employ vacuum tubing 120 which has an increasing diameter away from scalpel 10. A trade off must be made between making the diameter of tubing 120 at scalpel sufficiently large to achieve the necessary flow rates while not making it so large as to be unduly cumbersome for the surgeon. This balance can be achieved by gradually increasing the inner diameter of tubing 120 toward the vacuum source 140,150, thereby minimizing system pressure loses. Alternatively, a plurality of tubes of different diameters could be employed in a stepped series fashion so as to achieve this same result. In the preferred embodiment, PVC tubing is employed with a 7 mm inner diameter at the evacuator 10 progressively enlarging to a 0.375 inch (1.0 cm.) inner diameter at the filter 130. Tubing made of other materials, such as silicone rubber, could also be employed. Flex tubing 122 with an inner diameter of about 1.0 inch (2.5 cm.) is then used to connect filter 130 to blower 140 or alternatively a wall suction source 150.

Smoke evacuation system 110 is designed to provide an optimal balance between efficient evacuation and minimizing interference with use of the scalpel. It has been determined that the vacuum flow rate which is necessary for efficient evacuation of smoke during electrocauterization is much higher than previously predicted. Prior estimates operated under the assumption that tissue is dehydrated. In reality, the tissue is completely hydrated, and the moisture contained within tissue cells becomes instantly converted to steam during cutting or cauterizing. This steam tends to jet sporadically with high velocity as cell walls burst, entraining smoke within the jets. As a result, it has been determined that a vacuum flow rate of at least between 3.0 and 5.0 cubic feet per minute (85 and 140 l.p.m.) is necessary to efficiently evacuate the smoke and steam produced. Generally, 80% or greater evacuation would be considered acceptable. With the coaxial inlet 40 of the present invention, smoke can be efficiently evacuated with an inlet diameter 92 of between 0.30 and 0.60 inches (0.75 and 1.5 cm.), so as to achieve a maximum inlet flow velocity estimated to be about between 30 and 100 feet per second (9.0 and 30.0 m/s). The distance between leading edge 90 of inlet 40 and distal tip 33 of blade 32 is preferably about between 1.0 and 1.5 inches (2.0 and 4.0 cm.) in order to achieve optimal evacuation with the specified flow rate, while minimizing visibility interference for the surgeon. In the preferred embodiment, suction flow rate is between 4.0 and 4.5 cubic feet per minute (110 and 130 l.p.m.) and inlet diameter 92 is about 0.45 inches (1.1 cm.), which results in an inlet flow velocity estimated to be about between 50 and 75 feet per second (15 and 23 m/s). The distance of leading edge 90 from distal tip 33 of blade 32 is 1.25 inches (3.2 cm.) in the preferred embodiment.

Vacuum suction can be provided by a stand alone blower 140 or alternatively with a wall suction source 150, as shown in FIG. 4. Most hospital wall suction sources can provide only up to 3.0 cubic feet per minute (85 l.p.m.) flow rate. Therefore, two such sources 150 with a regulator to achieve the preferred flow rate would be necessary to achieve the desired flow rate.

It is desireable to "slave" the activation and deactivation of the smoke evacuation system 110 to the activation or deactivation of the electrosurgical device 20. This eliminates potentially irritating suction noise when the electrosurgical device 20 is not in use. Thus, for example in the case of an electrocautery scalpel, when either the "cut" or "cauterize" buttons 28 are depressed, the smoke evacuation system 110 provides suction to evacuator 10. When the button 28 is released, suction flow is subsequently cut off. It is preferred that the shutting off of flow is delayed for a period of time sufficient to clean up any residual smoke.

In the present invention, the automatic smoke evacuation system 110 slaves the activation or deactivation of the system to whether a current is sensed in power cord 30 of an electrosurgical device 20, as shown in FIG. 4. This approach permits the evacuation system 110 to be adapted to an existing electrosurgical device, without requiring a modification to the circuitry of power controller 112 for device 20. Current in power cord 30 can be sensed using a variety of known devices. In the preferred approach a radio frequency (RF) sensor 114, which senses electromagnetic energy, is employed. RF sensor 114, through antenna 115, receives the radio frequency waves emitted from power cord 30 when a current is passing therethrough. RF sensor 114 is appropriately placed near controller 112, and is tuned at 0.5 MHz in the preferred embodiment. This frequency is chosen to tune RF sensor 114 to the frequency of the electromagnetic energy in power cord 30 and to reduce sensitivity to AM band radio frequencies. The preferred RF sensor 114 is a radio frequency coil which is tuned to resonate at a particular frequency, in this case 0.5 MHz. Examples of other current sensing devices which could be used include loop type inductive sensors, Hall effect sensors, and capacitive sensors.

Figure 5:
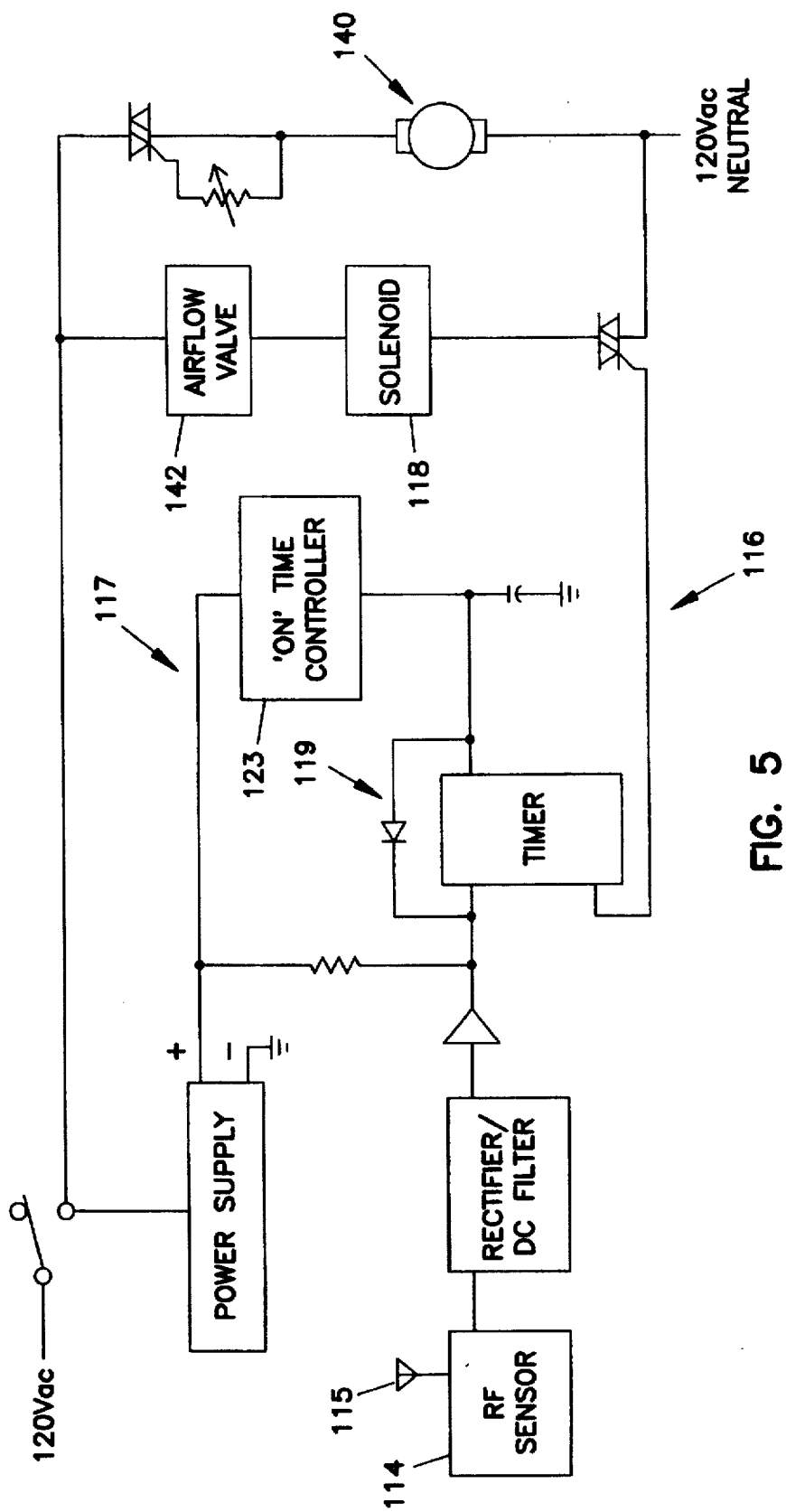
FIG. 5 is a circuit diagram of a switch mechanism for an automatic smoke evacuation system according to the present invention.

Referring to FIGS. 4 and 5, current sensor 114 is connected to switch circuit 116 which includes time delay circuit 117. Switch circuit 116 operates solenoid 118 which moves valve 142 to an open or closed position as appropriate. The wiring diagram of the automatic system is shown in FIG. 5. Time delay circuit 117 includes reset circuit 119, which resets the time delay in the event that a current is sensed during the time delay period. This assures that the full reset time delay exists whenever the electrosurgical 20 instrument is deactivated. In the preferred embodiment, this time delay can be varied from between 1 to 10 seconds using control potentiometer 123.

The valve which is moved by solenoid 118 in the preferred embodiment is a sleeve valve 142 at the inlet of blower 140, as shown in FIG. 4. It will be understood that the automatic system 110 could also be arranged to operate a valve connected to other suction sources, such as a wall suction source. Sleeve valve 142 consists of a plurality of circumferentially spaced slots 143 which correspond to slots in the inlet duct of blower 140. Solenoid 118 operates to rotate sleeve valve an appropriate number of degrees to line up the slots 143, thereby bypassing the majority of suction flow. These slots 143 should preferably have a total open area which is at least a factor of 1.5 to 2.0 greater than the cross sectional area of the inlet duct. The preferred valve 142 is acoustically treated with a 1.0 inch (2.5 cm.) thick open-cell urethane foam having a random noise reduction coefficient (NRC) of approximately 0.75. Other valve designs could also be used, as for example a three-way "Y-type" valve. In normal operation, blower 140 will be run throughout the procedure, and opening and closing of sleeve valve 142 will therefore immediately turn suction to instrument 20 off and on.

Figure 6:
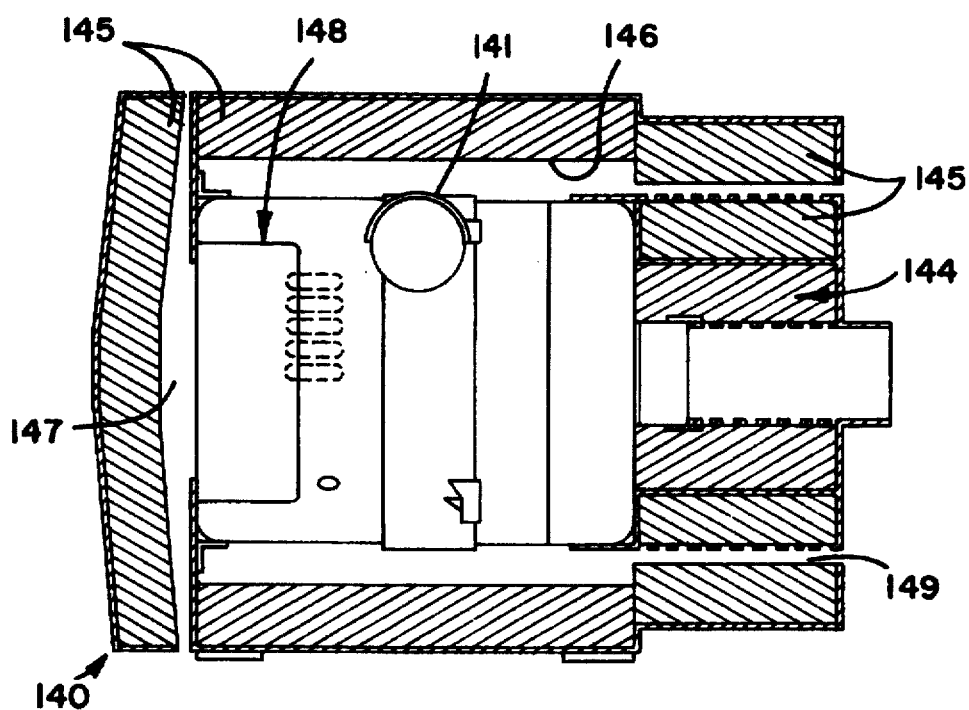
FIG. 6 is a cross-sectional view of a vacuum blower for the system of the present invention.

Referring to FIG. 6, the preferred blower 140 is shown. Blower 140 is an AMETEK No. 116566-13 vacuum blower which is acoustically treated to minimize noise in the operating room. The inlet is acoustically treated with a packed expansion can 144. The cooling air motor 148 is acoustically and aerodynamically isolated from the combined blower and cooling air exit annulus 149 to prevent the cooling motor 148 from over-heating. Following preferred practice, the height of chamber 146 is approximately one-half the diameter of the blower outlet 141 to minimize back pressure. Similarly, the same preferred ratio is employed for the cooling motor air inlet 147 relative to the cooling fan inlet (not shown). Air passes through expansion chamber 146 and exits blower 140 through annulus 149. Annulus 149 has a length to gap ratio of approximately 10 to provide optimal noise attenuation. The acoustical insulation 145 employed is preferably 1.0 inch (2.5 cm.) thick urethane open cell acoustical foam with a preferred NRC rating of approximately 0.75.

Figure 7:
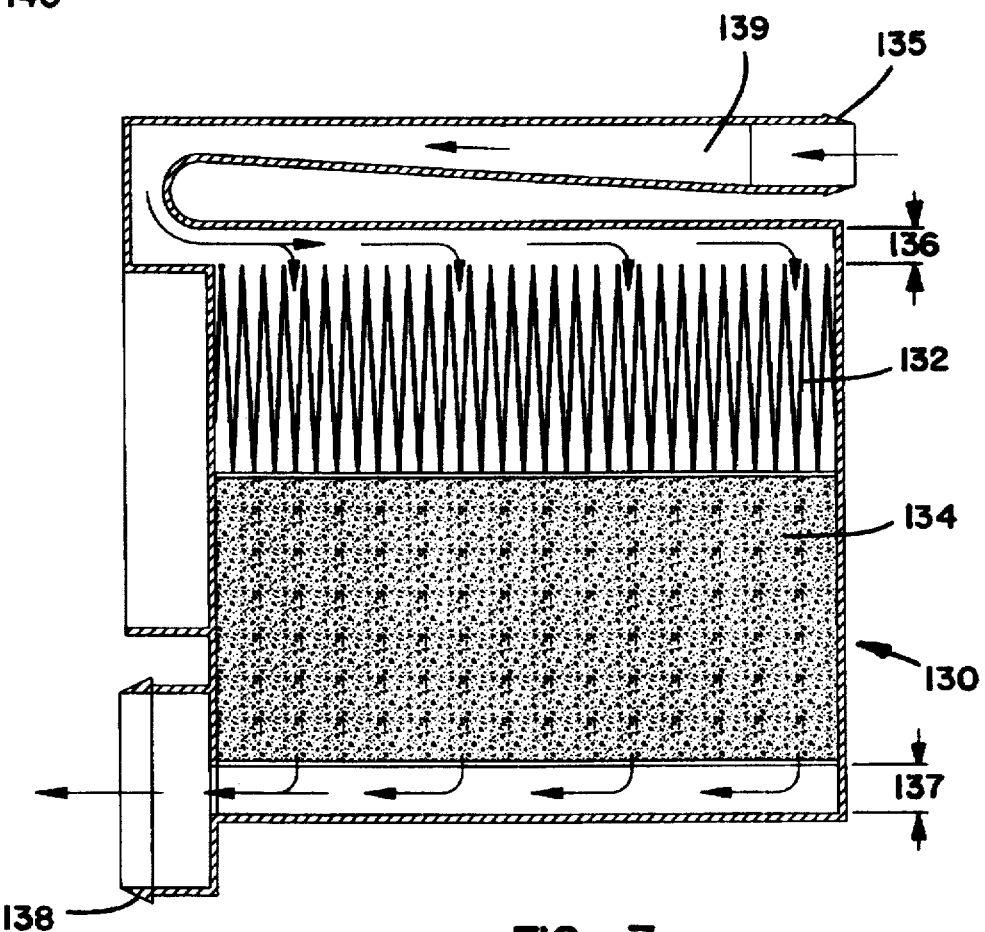
FIG. 7 is a cross-sectional view of a filter for the system of the present invention.

Referring to FIG. 7, a filter 130 for use in the preferred system is shown. Filter 130 includes particulate filter 132 capable of filtering particles in the 0.2 to 0.7 μm range, and a granular activated carbon absorption bed 134 sufficient to eliminate odors for a period estimated to be approximately 30 minutes of actual operational use. The preferred geometry provides a uniform flow distribution across the media 132, 134 so as to maximize their use. This is accomplished when the ratio of the outlet header height 137 to the inlet header height 136 is approximately between 1.40 and 1.80, preferably about 1.57. inlet 135 and outlet 138 are appropriately connected to vacuum tubing 120 and flex tubing 122, respectively, as shown in FIG. 4. The preferred inlet chamber 139 is tapered (not shown) in the downstream direction to a larger width. Filter 130, along with vacuum tubing 120 and evacuator 10, are intended for one-time use, and therefore everything upstream of flex tubing 122 is replaced with each use.

It should be understood that the present invention is not limited to the preferred embodiments discussed above, which are illustrative only. Changes may be made in detail, especially in matters of shape, size, arrangement of parts, or material of components within the principles of the invention, to the full extent indicated by the broad general meanings of the terms in which the appended claims are expressed.

What is claimed is:

1. A smoke evacuator for use with an electrocautery scalpel comprising a housing having fore and aft portions and upper and lower sides, at least one control button on the upper side, and a blade extending longitudinally from the fore portion, said smoke evacuator comprising:
   (a) a generally tubular nose portion adapted to extend over the fore portion of the scalpel and to have an inlet generally coaxial with the blade; and
   (b) an offset duct in fluid communication with and extending from said nose portion and adapted to extend at least partially along the lower side of the scalpel toward the aft portion of the scalpel;
   (c) said nose portion having a fore portion engagement sleeve defining an engagement opening for receiving the fore portion of the scalpel, said opening having a resilient material for sealing said opening with the fore portion of the scalpel;
   (d) said offset duct extending from said nose portion proximate said engagement opening, said engagement opening including upper and lower ends and being generally elliptical in shape, with said upper end forward of said lower end, so as to provide a smooth transition between said engagement sleeve of said nose portion and said offset duct.

2. The smoke evacuator of claim 1, wherein said resilient material in said engagement opening comprises compressible plastic formed as part of the smoke evacuator.

3. The smoke evacuator of claim 1, wherein said resilient material in said engagement opening comprises a separate sealable gasket bonded in said opening.

4. The smoke evacuator of claim 1, wherein said offset duct is adapted to extend to the aft portion of the scalpel and to attach to a power cord with a clip.

5. The smoke evacuator of claim 1, wherein an aft end of said offset duct is adapted to terminate at approximately a center of the scalpel.

6. The smoke evacuator of claim 1, further comprising a swivel proximate an aft end of said offset duct for rotatably connecting said offset duct to a vacuum tube.

7. The smoke evacuator of claim 1, wherein said offset duct is adapted to be attached to the scalpel by an adjustable ratchet connected to a power cord of the scalpel.

8. The smoke evacuator of claim 1, wherein said evacuator further comprises a nose extension attachable to said nose portion so as to make said evacuator compatible with an extended blade used in the scalpel.

9. A smoke evacuator attached to an electrocautery scalpel comprising a housing and a blade extending longitudinally therefrom, said smoke evacuator comprising:
   (a) an annular nose defining an inlet proximate the blade, said inlet having an inlet diameter;
   (b) vacuum tubing in fluid communication with said inlet; and
   (c) means for creating a vacuum through said tubing and in said inlet;
   (d) said annular nose having a radiused leading edge on an inner side, the ratio of said radius to said inlet diameter being about between 0.15 and 0.25.

10. The smoke evacuator of claim 9, wherein said annular nose is generally coaxial with the blade and said inlet diameter is about between 0.30 and 0.60 inches.

11. The smoke evacuator of claim 10, wherein said vacuum means provides a suction flow rate of about between 3.0 to 5.0 cubic feet per minute and said leading edge of said annular nose is about between 1.0 and 1.5 inches from a distal tip of the blade.

12. The smoke evacuator of claim 10, wherein the ratio is approximately 0.18 and the inlet diameter is approximately 0.45 inches.

13. The smoke evacuator of claim 9, wherein said tubing between said annular nose and said vacuum means is progressively increased to a larger diameter toward said vacuum means.

14. A smoke evacuator attached to an electrocautery scalpel comprising a housing and a blade extending longitudinally therefrom, said smoke evacuator comprising:
   (a) an annular nose defining an inlet proximate the blade;
   (b) vacuum tubing in fluid communication with said inlet;
   (c) means for creating a vacuum through said tubing and in said inlet; and
   (d) a plurality of axially outwardly and radially inwardly turned ribs spaced around the circumference of said annular nose;
   (e) whereby said ribs prevent unintentional suckdown on tissue in the vicinity of said inlet.

15. The smoke evacuator of claim 14, wherein said ribs comprise a single part which is selectively attachable to said annular nose.

* * * * *